(12) United States Patent
Bosboom et al.

(10) Patent No.: US 9,469,026 B2
(45) Date of Patent: Oct. 18, 2016

(54) MOTOR SYSTEM, MOTOR, AND ROBOT ARM DEVICE COMPRISING THE SAME

(75) Inventors: Dennis George Hugo Bosboom, Nutterden (DE); Johannes Jacobus Fütterer, Beuningen (NL); Johan Bosboom, Vriezenveen (NL)

(73) Assignee: SOTERIA MEDICAL B.V., Arnhem (NL)

( * ) Notice: Subject to any disclaimer, the term of this patent is extended or adjusted under 35 U.S.C. 154(b) by 333 days.

(21) Appl. No.: 13/988,545

(22) PCT Filed: Nov. 22, 2010

(86) PCT No.: PCT/EP2010/067947
§ 371 (c)(1),
(2), (4) Date: Jul. 30, 2013

(87) PCT Pub. No.: WO2012/069075
PCT Pub. Date: May 31, 2012

(65) Prior Publication Data
US 2014/0076087 A1    Mar. 20, 2014

(51) Int. Cl.
*B25J 17/00*     (2006.01)
*B25J 9/10*      (2006.01)
*F16H 21/44*     (2006.01)
*A61B 10/02*     (2006.01)
*A61B 10/04*     (2006.01)
(Continued)

(52) U.S. Cl.
CPC .............. *B25J 9/1035* (2013.01); *A61B 34/30* (2016.02); *F16H 21/44* (2013.01); *A61B 10/0233* (2013.01); *A61B 2010/045* (2013.01); *A61B 2017/00991* (2013.01); *A61B 2017/3409* (2013.01); *A61B 2034/304* (2016.02); *Y10T 74/18984* (2015.01); *Y10T 74/20305* (2015.01)

(58) Field of Classification Search
CPC ........ B25J 9/1035; B25J 9/126; F16H 21/44
USPC .............. 74/490.01, 490.03, 490.04, 490.05, 74/107; 606/80, 130
See application file for complete search history.

(56) References Cited

U.S. PATENT DOCUMENTS 3,552,220 A * 1/1971 MacDermod ................... 74/107
4,742,614 A * 5/1988 Mack et al. ..................... 29/785
(Continued)

FOREIGN PATENT DOCUMENTS

DE           29803411 U1    8/1998

OTHER PUBLICATIONS

International Preliminary Report on Patentability and Written Opinion for corresponding international patent application No. PCT/EP2010/067947 dated May 22, 2013.
(Continued)

*Primary Examiner* — William Kelleher
*Assistant Examiner* — Zakaria Elahmadi
(74) *Attorney, Agent, or Firm* — Harness, Dickey & Pierce, P.L.C.

(57) ABSTRACT

The present invention is related to a motor system, a motor, and to a robot arm device comprising the same. According to the invention, a motor is provided comprising a rack having a periodic surface thereon which is engaged by a plurality of engaging elements. By driving the engaging elements back and forth towards the surface structure in a periodic and time shifted manner, a linear motion can be brought about.

13 Claims, 6 Drawing Sheets

(51) Int. Cl.
  *A61B 17/00* (2006.01)
  *A61B 17/34* (2006.01)

(56) References Cited

U.S. PATENT DOCUMENTS

| | | | |
|---|---|---|---|
| 5,410,638 A | 4/1995 | Colgate et al. | |
| 7,748,672 B2* | 7/2010 | Walke | 248/207 |
| 2006/0018796 A1* | 1/2006 | Sitte | 422/100 |
| 2007/0034046 A1* | 2/2007 | Stoianovici et al. | 74/640 |
| 2008/0269741 A1* | 10/2008 | Karidis | 606/56 |
| 2009/0035739 A1* | 2/2009 | Alemzadeh | 434/264 |
| 2009/0259122 A1* | 10/2009 | Larson et al. | 600/411 |
| 2010/0122602 A1* | 5/2010 | Marcroft | B25J 17/0216 74/490.03 |
| 2010/0305568 A1* | 12/2010 | Ross et al. | 606/56 |
| 2012/0180593 A1* | 7/2012 | Alet et al. | 74/490.07 |

OTHER PUBLICATIONS

International Search Report PCT/ISA/210 for PCT/EP2010/067947 dated Aug. 12, 2011.
Written Opinion PCT/ISA/237 for PCT/EP2010/067947 dated Aug. 12, 2011.

* cited by examiner

FIG. 7

MOTOR SYSTEM, MOTOR, AND ROBOT ARM DEVICE COMPRISING THE SAME

The present invention is related to a motor system, a motor, and to a robot arm device comprising the same. More in particular, the present invention is related to motors offering high precision during linear motion, and which are moreover suitable to be used in a medical environment.

Several types of motors have been developed for linear motion. For instance, linear motors are used for accurate positioning of wafers in the semiconductor industry. Another example is a rack and a pinion. The pinion is circular and is provided with teeth on its outer surface. These teeth engage other teeth which are disposed on a linear bar, i.e. the rack. In this way, rotary motion of the pinion is converted into linear motion of the rack.

A particular interesting application for a motor and robot arm device is the area of medical imaging using magnetic resonance imaging (MRI).

Due to the progressive ageing of the population there are an increasing number of new cases of cancer. If cancer is discovered early, the chance of recovery is greater. New diagnostic methods make it possible to detect cancer at a very early stage.

A frequently occurring form of cancer is prostate carcinoma. A method for early detection makes use of contrast-enhanced MRI of the prostate. Irregularities in the prostate, which could indicate cancer, are hereby detected. For definitive diagnosis and thereby the start of treatment, a biopsy tissue sample is however necessary. The problem of the increasing diagnostic quality of the MRI examinations is that lesions are found which are so small that they are overlooked with conventional biopsy techniques. This results in the biopsy having to be repeated time after time or, worse still, in the conclusion being drawn that there is no cancer while the lesion has been missed by the biopsy needle.

For this reason there is a need for being able to take biopsy samples in accurate, verifiable, simple and rapid manner on the basis of the MRI imaging. It would be optimal if the biopsy needle could be manipulated under MRI view, wherein deformation of the prostate due to manipulation of the needle can be compensated during the procedure. Only when the needle is seen in the lesion, and it is thereby demonstrated that a biopsy sample has been taken from the suspect site, can a definitive judgment be made as to whether or not cancer is present. The present methods based on MRI are MRI-verified instead of MRI-guided and thus require a great deal of time. The physician must enter the MRI space, slide the patient out of the MRI, operate the needle, after which the patient must be pushed back into the MRI. The physician leaves the space and a verification MRI is made. This is repeated until the needle has arrived at the desired location.

Hence, there is a need for motors to allow accurate positioning, in particular for medical devices.

Another need arises from the fact that these motors need to be sterile.

In addition, these devices need to be suitable for operation within an MRI environment.

It is an object of the invention to address at least one of the above mentioned needs.

According to the present invention, this object is achieved with a motor system that comprises a motor having a rack member provided with a structure on a surface thereof, said structure having a periodic arrangement of a gear element in at least one direction. A one-dimensional example of a rack member is the aforementioned rack, in which the surface structure comprised a periodic arrangement of teeth. However, two or more dimensional arrangements are also possible for instance in the form of a metal plane provided with a honeycomb type configuration of dimples in its surface. Such a surface is characterized by more than one direction in which a periodic arrangement of the gear element, in this case being a single honeycomb cell, can be identified.

The motor according to the invention further comprises a tooth member which accommodates a set of multiple actuators arranged for one direction of said at least one direction, each of said actuators comprising an engaging element shaped for engaging said gear element and a drive unit for powering said engaging element to move back and forth with respect to said periodic structure.

According to the invention, a set of actuators is used for one of the directions along which a periodic arrangement can be identified. Multiple sets can be used for different directions.

The engaging element is shaped for engaging the gear element. Preferably, the engaging element has an outer surface for contacting the gear element which displays at least a part of a form complementary to the gear element itself. In case of the known rack and pinion, a tooth of the pinion forms the engaging element whereas the circular structure and the driving means for rotating the circular structure can be regarded as comprising the drive unit.

According to the invention, the engaging element engages said gear element at least during part of the movement towards the gear element to cause a relative movement between said rack member and said tooth member in said one direction of said at least one direction. Hence, engagement between the gear element and the engaging element causes a relative motion between the tooth member and the rack member, meaning that one of those members is stationary or that both of them are non-stationary.

In general, the engaging element engages the rack member from a particular direction not being the direction of the resulting relative motion. In a rack and pinion, the force required for linear motion is induced directly by the rotary motion of the pinion. With the present invention, the pushing force is a result of the shape of the engaging element and the gear element in combination with the force in the direction of engagement.

With the present invention, each of said actuators is positioned spaced apart to engage said periodic structure at a different reduced phase thereof. Here, different phase should be construed as engaging the periodic structure at a different position along the direction of the periodic arrangement.

The motor system of the invention further comprises a control unit for periodically controlling each drive unit of each actuator in the set of actuators to operate in a time-shifted manner with respect to each other. Consequently, each of the actuators in a given set moves periodically by itself. In addition, the motion of a given actuator is time-shifted with respect to another actuator in the same set meaning that the actuators are not in phase. For instance, there will be times when one of the actuators is moving towards the periodic structure whereas another actuator is moving away. The actuators will preferably be driven with the same period.

According to the present invention, periodically controlling each drive unit allows for a continuing relative movement in said one direction of said at least one direction during a plurality of control periods. Here, continuing movement refers to the situation in which movement is always in a given direction and not in the opposite direction.

Unlike the aforementioned rack and pinion, the motor according to the invention displays a plurality of actuators, each with an engaging element and drive unit, wherein the drive units are individually controllable.

The relative motion between the rack member and the tooth member for a single action of a single actuator is determined by the shape of the gear element and the shape of the engaging element. It therefore becomes possible to achieve a high accuracy in linear motion. For instance, a relatively steep profile can be used in combination with a relatively large number of actuators. The relatively small displacement achieved by a single actuator is then compensated for by the larger number of actuators in a single set. If a similar accuracy is to be achieved with a rack and pinion, the size of the pinion and/or the size of the teeth need to be decreased, resulting in a less stable system due to the reduced area of engagement between rack and pinion.

Preferably, said gear element, the number of actuators in the set of actuators, said control unit, and said actuator positioning are configured such that the relative movement between the tooth member and the rack member equals or exceeds the length of the gear element in said one direction of said at least one direction after the control unit has controlled each of said actuators for one period of said periodic control. Advantageously, each engaging element is driven using the same time period. Furthermore, each engaging element preferably infers an identical relative displacement between rack member and tooth member.

According to the invention, the sum of the individual displacements resulting from the different actuators exceeds the length of the gear element in the direction of motion. Because of this, each engaging element can move back and repeat its action thereby allowing the continuing relative movement.

Preferably, the set of actuators is positioned spaced apart along said one direction of said at least one direction. By arranging the actuators in the direction of motion, mechanical forces not relevant for the motion of interest can be avoided thereby avoiding wear and friction within the motor itself.

The arrangement of the gear element is preferably periodic in at least two dimensions, wherein the actuator further comprises a set of actuators for each of said at least two dimensions. In this embodiment, the rack element can be construed as a multi-dimensional extension of the known rack. At least two sets are arranged in the motor, each for a different direction of periodicity. Not every possible direction of periodicity needs to be addressed by a set of actuators. Still, using two sets for two different directions allows relative motion in two different directions. Moreover, because the periodicity is generally different in these directions, the speed associated with the relative motion in those directions differs accordingly.

It should be understood by the skilled person that movement in any desired direction can be obtained by using a suitable arrangement of gear elements and a suitable arrangement of engaging elements. In fact, any direction in which the arrangement is periodic can be used for this purpose. Furthermore, the fact that the arrangement is periodic does not necessarily implicate that the engaging elements are arranged to engage neighbouring gear elements. Moreover, the total number of engaging elements depends on the shape of the gear element and the shape of the engaging element. Together, they determine the shift of the rack member due to mutual engagement. The combined shift due to all engaging elements should be sufficient to move the rack member over the length of the gear element.

To that end, it is advantages if the control unit is arranged to switch from controlling the actuators belong to a set to controlling the actuators belonging to a different set. In this way, the separate motions can be achieved consecutively.

Apart from arranging the gear element on a flat surface of the rack member, or on a curved surface thereof, the rack member itself could also comprise a body having the gear element periodically arranged around it, preferably completely. With such a motor, the relative motion could cause the rack member and tooth member to rotate and/or translate relative to each other. By having the gear elements wrapped around the rack member, so that a continuous surface structure is formed, the rotation can be complete such that after a complete rotation, the engaging elements are positioned at the same reduced phase. Depending on the positioning of the engaging elements relative to the rack member, and the periodic arrangement of the gear elements, this rotation may be accompanied by an axial displacement. Hence, depending on the arrangement of the engaging elements and the arrangement of the gear elements, the rack member may rotate or translate or simultaneously rotate and translate. Choosing a different arrangement of the engaging elements allows movement in different directions.

A particular suitable shape of the rack member is a substantially cylindrical shape in which the periodic arrangement is on a circumferential surface of said cylinder, i.e. on the surface extending in parallel to the axis of the cylinder. Here, the tooth member comprises a housing provided with a circular opening for receiving at least part of said rack member, and the set of actuators is arranged in a radial direction with respect to said rack member. Also here, the rack member or the tooth member can be stationary by securing it to a supporting frame.

In the aforementioned embodiment of the present invention, comprising the cylindrical embodiment of the rack member, the circular opening can be formed by a circular through hole in said housing. This allows a large dynamic range of the motion. For instance, if the tooth member is stationary, the rack member can move substantially over its full length. Movement limiters can be arranged on the rack member and/or the tooth member to prevent the rack member from getting disengagement with the tooth member.

Additionally or alternatively, the gear element is distributed in a helical path around said cylindrical shape. In this situation the direction of movement is the tangent vector to the helical path. Stating that the actuators are positioned in the direction of relative movement then implies that they are positioned at similar radial positions but different axial and circumferential positions, the latter positions corresponding with the relevant tangent vector.

To improve stability of the motor, the rack member and the tooth member can be fixed with respect to each other in a direction perpendicular to the surface structure. For instance, with the cylindrical rack member embodiment, the radial distance between the rack member and tooth member is fixed, as the radial direction is perpendicular to the surface structure. A supporting frame may be used to secure one of the tooth member and the rack member, whereas the other member is free to move in the one direction of said at least one direction.

Advantageously, the motor further comprises a guide element disposed in the rack member and/or the tooth member for guiding the other of the rack member and/or the tooth member therein. With the cylindrical shape embodiment, such guide is formed by the circular opening or through hole as this guides the tooth member along its axis.

To avoid any clearance of the motor, it is advantageous if the control unit is arranged to control the drive units within the set of actuators such that at least one powered engaging element engages the surface structure at each point in time during operation of the motor. In this way, there is always direct engagement between an engaging element and a gear element. Sudden external pushes exerted on one of the non-stationary parts, for instance the cylindrical rack element, does not necessarily result in a displacement of the rack element as the external push is countered by the continuous engagement between engaging element and tooth member.

Additionally or alternatively, the drive unit of each actuator is configured to operate in a powering state for powering said engaging element to move towards said rack member and in a release state for movement of said engaging element away from the rack member, said drive unit comprising a resilient member at least operable in said release state and configured for urging the engaging element to move away from the rack member and/or the drive unit being configured to allow the engaging element to move away from the rack member in the release state essentially without exerting a force on the engaging element. Hence, either the engaging element is actively withdrawn from the position in which it engages the rack member or it is allowed to move back essentially without a counter force being present. The latter enables a moving rack member to push away the engaging element in the release state. In any case, the resistance encountered by the rack member exerted by actuators moving away from the periodic structure should be avoided.

It is preferred to have the control unit arranged to control the actuators of the set sequentially.

The gear element is preferably symmetric from the viewpoint of said actuators, and the control unit is preferably further capable to control said actuators of said set to cause a relative movement between the rack member and the tooth member in a direction opposite to said one direction of said at least one direction.

By having a symmetric gear element, i.e. the same structure is encountered moving in a particular direction and in the direction opposite thereof, relative motion can be achieved in two opposite directions, e.g. from left to right and from right to left. The control unit determines which direction is used by adapting the control scheme for the individual actuators.

Within the context of the present invention, a direction and a direction opposite to the former direction should be construed as being different directions, each being possibly assigned to a different set of actuators. However, by having a symmetrical gear element it is possible the use the same set for both directions.

Preferably, the gear element comprises a conical cavity in the surface of said rack member and the engaging element has a corresponding conical protrusion. The conical shape or another shape which is rotation symmetric in a direction perpendicular to the surface structure, provides a self centering engagement between the engaging element and the gear element. This reduces wear of the system and ameliorates the required accuracy for the positioning of the actuators.

In an embodiment, the set of actuators for a given direction of periodicity comprises at least n actuators, wherein n is larger than or equal to two, and wherein the respective actuators are positioned to engage the surface structure at a reduced phase of approximately $m \times 360/n$, wherein $m=1 \ldots n$, respectively. Here, reduced phase refers to the phase of at a certain position of the periodic structure corrected for the integral numbers of periods contained therein. For instance, an absolute phase of 480 degrees would result in a reduced phase of 480−360=120 degrees.

It is important to calculate the periodicity from a direction of engagement. If the engaging elements engage the periodic structure for instance at an angle, it is possible, as seen from the engaging elements, for the relevant length of a gear element to be other than in the case of perpendicular engagement. In this case it is recommended to use the former length for calculation purposes.

The actuators at different but equidistant reduced phases are preferably aligned with respect to different gear elements. This prevents the actuators to be spaced too closely together where they would obstruct each other's movement. Furthermore, the actuators are preferably positioned such that the engaging elements engage the surface structure perpendicularly.

Although a different set is attributed to each direction of periodicity, this does not exclude the possibility that at least one actuator belongs to two distinct sets of actuators. For instance if 5 actuators are arranged in a cross-like structure, the actuator in the middle of the cross would be involved in movement in both directions indicated by the cross.

An advantageous embodiment of the drive unit comprises an actuable piston-type cylinder, said actuable cylinder having a cylinder housing and a piston movable therein, wherein said engaging element is formed by and/or arranged on an end of said piston. Here, the cylinder housing is stationary with respect to gear element in the direction of engagement.

The drive unit could comprise other suitable means for driving the engaging element. In addition to the abovementioned cylinder, e.g. hydraulic or pneumatic, electrical motors, such as a linear motor, may be used.

Such actuable cylinder is preferably single-acting. This means that motion of the piston towards the gear element is due to actuation of the cylinder, thereby exerting a significant force onto the gear element, whereas the reciprocal movement away from the gear element is caused by some sort of resiliency of the cylinder or external thereto. For instance, a spring or other resilient element, such as fluid pressure, could be arranged within the cylinder housing urging the piston to move back when it is not actuated. During movement away from the gear element, the piston exerts no or very little force onto the gear element.

Especially for medical environments, it is preferred to use pneumatic cylinders as the actuable cylinders. Hydraulic cylinders, or other cylinders, introduce the risk of leakage. The activation of the pneumatic cylinders preferably takes place using compressed air, although it is also possible to make use of underpressure.

The pneumatic cylinders are preferably pulse-operated during operation. The cylinder will here be activated for a short time. The speed of the relative movement of the tooth member and the rack member can be determined by the speed at which the pneumatic cylinders are activated and the compressed air pressure used.

To further make the motor of the invention suitable for medical environments, and MRI environments in particular, it is convenient to fabricate the motor out of non-conductive non-magnetized or non-magnetisable material.

According to a second aspect, the present invention provides a robot arm device, comprising a first frame part which can be mounted or placed on a support for the robot arm device, and a second frame part coupled to the first frame part. Here, the motor according to the invention is used for changing the mutual orientation and/or distance of the first and second frame part. To that end, the tooth member of said motor is coupled to one of said first and second frame part, and the rack member is coupled to the other of said first and second frame part. This coupling need not be direct but can be embodied through hinges or other intermediate structures.

The first and/or second frame part can comprise a flat plate part for easy placement of components thereon. The first frame part can for instance thus be attached to a bed on which a patient is lying, thereby obtaining a stable whole.

The motors placed between the first and second frame parts form a structural part of the robot arm device.

In a preferred embodiment, the rack member, for instance in the form of the aforementioned cylinder, is connected to the second frame part. The tooth member is then connected to the first frame part. It is possible for the motor to be mounted the other way round. In the case that a plurality of motors are disposed between the frame parts, it is possible for the motors to be mounted mutually differently such that a combination of the two above mounting methods results.

The robot arm device preferably comprises at least six motors in accordance with the invention arranged to form a Stewart platform. This type of platform provides six degrees of freedom of movement, i.e. translation, angulation and rotation in all directions. The coupling between the motors on the first and second frame parts must support these degrees of freedom and hinges must be provided accordingly.

To be able to use the robot arm device, or the motor itself, within an MRI environment, it is preferred to use non-magnetic, non-magnetisable and non-conductive materials such as plastic, carbon, glass or ceramic material.

The robot arm device can be further improved if the first and/or second frame part is provided with a through hole for receiving the tooth member or the rack member of a motor therein. This is particularly interesting if the tooth member or the rack member itself comprises a through hole for accommodating the other of the tooth member or the rack member therein. Because of the through hole the tooth member or rack member can move through the other member thereby increasing the dynamic range of the motor. By arranging such motor in the through hole of the first or second frame part, the minimal distance between the two frame parts can be reduced as a large part of the motor can be arranged outside of the space between the first and second frame part.

To improve the robot arm device even further, it may comprise a hinge, preferably a ball joint, having a through hole provided therein in which said tooth member or said rack member is fixedly connected to said hinge, and wherein the hinge is arranged for hingedly connecting said tooth member or said rack member to said first and/or second frame part. This configuration not only allows reducing the minimal distance between the first and second part but also allows rotation of the motor. In case a ball joint is used, this rotation is possible over a plurality of axes.

According to a further aspect, the invention provides a motor as previously defined. The drive units of this motor are externally controllable.

Next, the invention will be discussed in more detail under reference to the accompanying drawings, wherein.

In the description of the embodiments that follow below, the operation of the motor is described as if the tooth member is kept stationary. The skilled person should understand that it is also possible to keep the rack member stationary.

Figure 1:
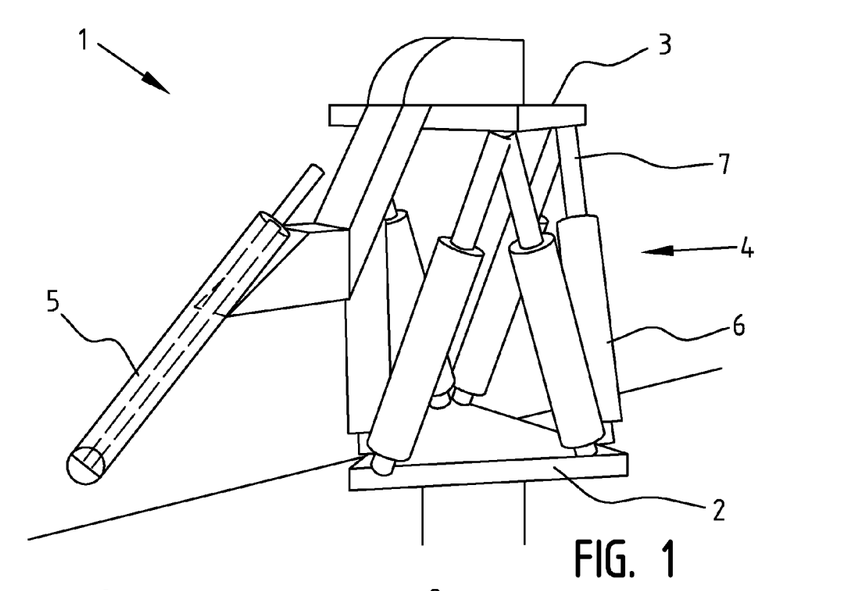
FIG. 1 shows a preferred embodiment of a robot arm device according to the present invention.

FIG. 1 shows an embodiment of robot arm device 1 according to the present invention. Robot arm device 1 comprises a first frame part 2 and a second frame part 3. Frame parts 2, 3 are mutually connected by means of motors 4. A medical aid is mounted on top of second frame part 3. In FIG. 1, this medical aid is a needle guide 5 which is attached by means of an arm.

The arrangement of the motors is in accordance with the Stewart platform principle. Motors 4 are here connected to frame parts 2, 3 by means of rotatable couplings (not shown), for instance ball (and socket) joints. Motors 4 comprise a tooth member in the form of a motor housing 6 in which a rack member in the form of a piston 7 is received movably.

The combination of motor housing 6 and piston 7 operates as a telescope and is referred to in the following as leg. Height, parallel displacement, rotation and angulation of the robot arm device are determined by varying the length of the different legs.

Figure 2A:
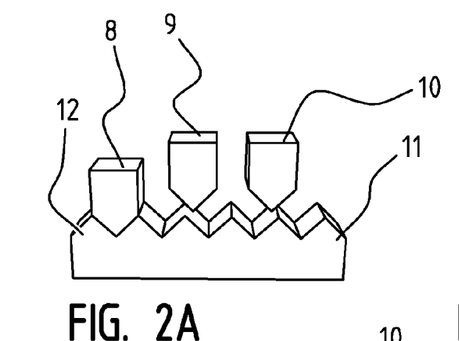
FIGS. 2A-2D show the principle of the motor according to the invention with three engaging elements.
Figure 2B:
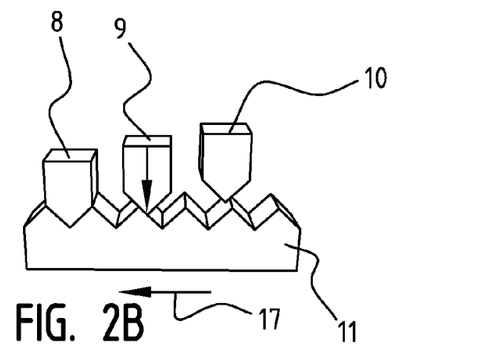
Figure 2C:
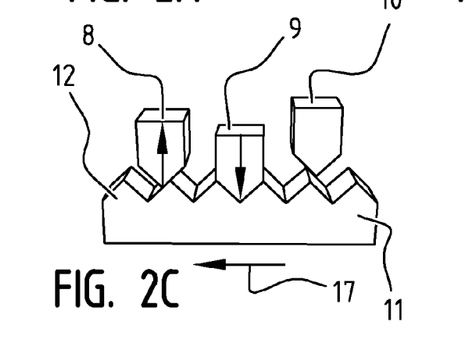
Figure 2D:
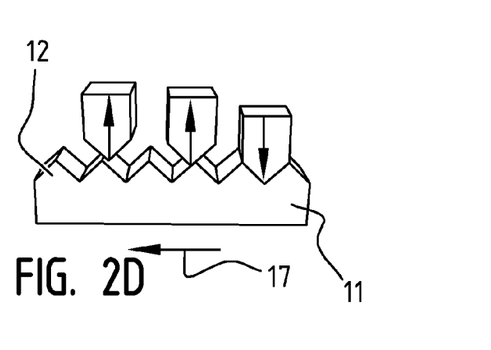

FIGS. 2A-2D show schematically a preferred embodiment of motor 4 according to the invention. Three piston-type cylinders are arranged in the tooth member. These cylinders comprise both an engaging element, in the form of teeth 8, 9, 10, and a drive unit (not shown), or part thereof. The cylinders are preferably pneumatic cylinders. Teeth 8, 9, 10 are formed similar to teeth of a toothed wheel. The three teeth are phase-shifted 120 degrees relative to the periodic structure on rack member 11. This periodic structure comprises a series of gear elements in the form of triangular teeth 12. As can be seen from the figure, the different teeth each are positioned at different reduced phases of the periodic structure. In FIG. 2A, taking the top of each triangle 12 as 0 degrees, tooth 8 has a reduced phase of 180 degrees, tooth 9 a reduced phase of 60, and tooth 10 a reduced phase of 300 degrees.

Starting with the situation shown in FIG. 2A, when tooth 9 is activated, tooth 8 is deactivated. Activation of a tooth means that the drive unit actuates the tooth to move towards the rack member. Deactivation means that the tooth withdraws. This can be accomplished either by a net force from the drive unit itself, e.g. a spring in the pneumatic piston driving the tooth, or by the interaction with the rack member. In this latter case, the rack member, being engaged by another engaging element, pushes the deactivated engaging element away from the rack member. In either case, it is important to minimize the force exerted by the deactivated engaging element on the rack member.

Due to the engagement of tooth 9, rack member 11 slides sideways. Tooth 8 is hereby actively pushed back, see FIGS. 2B and 2C. Tooth 10 slides from the left side of the top of the gear element to the right side. Hence, when tooth 9 has fully extended in rack member 11, tooth 10 is in the correct position to engage rack member 11.

Hence, if the teeth are activated alternately or sequentially, a stepwise displacement of rack member 11 is possible. This is possible at any desired speed by varying the rhythm of the teeth. If none of the teeth are activated, rack member 11 can move freely relative to teeth 8, 9, 10. If at least one tooth is continuously activated, rack member 11 is blocked. An advantage in continuously activating at least one tooth, or engaging element in general, is the reduced clearance of the motor that can be achieved. Due to the continuous engagement, the motor is less sensitive to forces exerted on the rack member.

Figure 3:
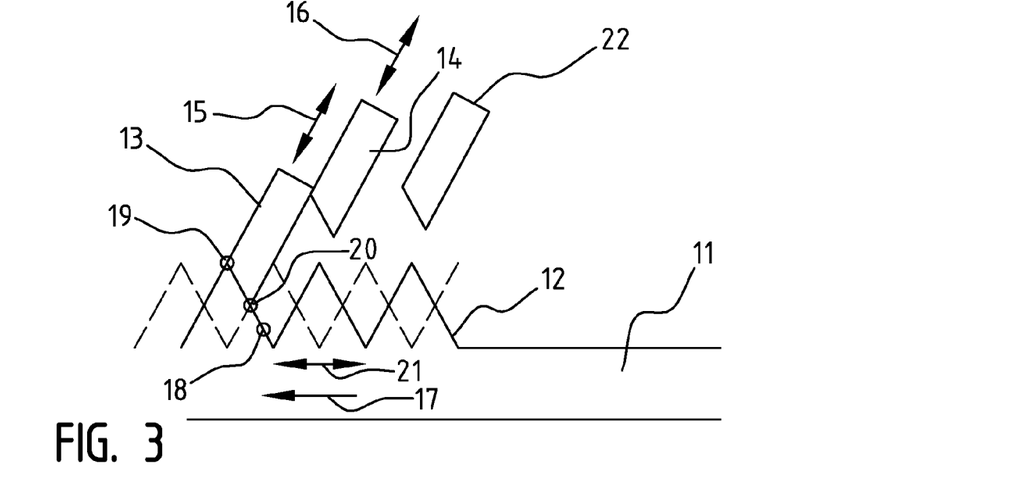
FIG. 3 shows a variation of the motor of FIG. 2A with two engaging elements.

FIG. 3 shows the general operating principle of a motor according to the present invention, making use of two piston-type cylinders.

FIG. 3 shows a rack member 11 comprising a series of teeth 12 placed one after another. Also shown are two teeth 13, 14 which are connected to separate piston-type cylinders, similar to the embodiment in FIG. 2A (not shown). Movement of these teeth is possible along the direction indicated with arrows 15, 16.

In FIG. 3, tooth 13 engages rack member 11, and more in particular the periodic structure on a surface thereof. As tooth 13 moves further downward when the corresponding cylinder is activated, rack member 11 will move as indicated by arrow 17. The position will hereby be taken up as shown in broken lines. As can be inferred from FIG. 3, tooth 14 can in this case engage rack member 11. The cylinder corresponding with this tooth is here activated and the cylinder corresponding to tooth 13 is deactivated or actively withdrawn. As a result, tooth 13 will move back, for example due to the spring forces related to a spring situated in the (single-action) cylinder itself.

Once tooth 14 has made its outward movement, rack member 11 has arrived at a position comparable to the starting position, and the procedure can be repeated. The cylinder of tooth 13 is then again activated, as opposed to the cylinder of tooth 14, which is deactivated.

It must be noted that the periodicity of gear rack 11, as seen from a direction perpendicularly thereof, is different from when seen from the direction of engagement of teeth 13, 14, this corresponding to arrows 15 and 16 respectively. The length of side 18 is relevant to the teeth.

Teeth 13, 14 are disposed at different reduced phases in FIG. 3. It can for instance be stated that tooth 13 corresponds to position 19 of rack member 11 and tooth 14 to position 20. These two positions have a phase difference of 180 degrees when this is calculated with side 18 as relevant dimension of the gear element. Clearly, this is different from calculating the reduced phase starting from the length indicated by arrow 21.

It must otherwise be noted that tooth 22, which is shown by way of illustration, has the same reduced phase as tooth 14.

This system enables movement in one direction. A second system can be used, although in mirrored position, for movement in the other direction.

Figure 4A:
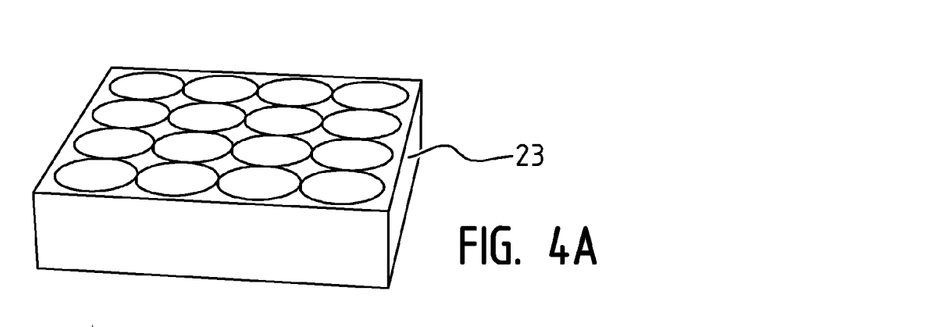
FIGS. 4A-4B show an embodiment of a rack member with a two-dimensional periodic structure.
Figure 4B:
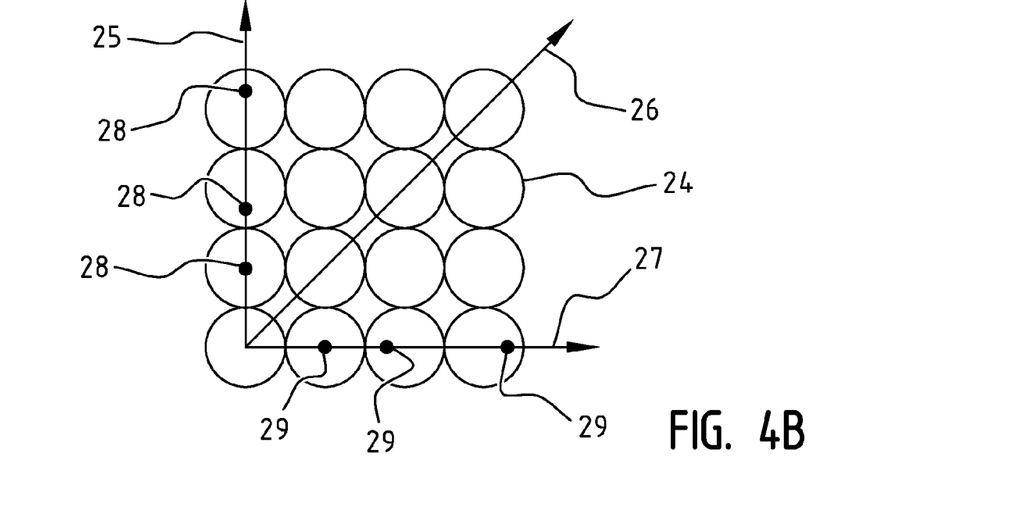

The embodiment in FIG. 4A shows a two-dimensional periodic structure on rack member 23. The periodic structure comprises a two-dimensional arrangement of conical holes 24 in an otherwise flat surface. To ensure optimal engagement, the engaging elements have a shape corresponding to the shape of the conical holes, i.e. conical protrusions. Due to the arrangement, several directions can be identified along which the structure is periodic. In FIG. 4B, several directions 25, 26, 27, are examples thereof.

By arranging the engaging elements in a suitable manner with respect to rack member 23, displacement of rack member 23 can be achieved along any of the directions 25, 26, 27. For instance, FIG. 4B indicates the location of the tip of each engaging element, by means of a dot, with respect to rack member 23. In FIG. 4B, two sets of actuators are indicated. A first set, comprising actuators of which tips of the engaging elements are indicated by dots 28, and a second set, comprising actuators of which tips of the engaging elements are indicated by dots 29. The first set is used for movement of rack member along direction 25, whereas the second set is used for movement along direction 27. If the two sets were arranged in a cross-like shape, one of the actuators could have been used for both movements, thereby saving costs and space.

It should be noted that directions 25, 26, 27 are not the only possible directions. For example, a further direction can be identified corresponding to one conical hole in one direction and two conical holes in a direction perpendicular thereto. This direction, corresponding to the motion of a knight in a chess game, also represents a direction in which a periodicity of the gear element arrangement can be identified. When using this direction, the engaging elements are not arranged to engage neighbouring conical holes. As described before, the length of the gear element depends on the direction that is chosen. For instance, with the above-mentioned knight like direction, the length of the gear element is the square root of five times the diameter of a conical hole squared. Sufficient engaging elements should be arranged to ensure that the rack member can move over the length of the gear element. It is further noted that the arrangement of the engaging elements need not be as depicted in FIG. 4B. For instance, the engaging elements might be distributed such that they are no longer in the line of motion and/or that they are no longer arranged adjacent to each other. However, each engaging element must have a prescribed phase difference with the gear elements underneath it to allow for the motion in a given direction.

In the embodiments of FIGS. 2, 3 and 4, rack member 11, 23 comprises a series of teeth/holes. The displacement of rack member 11, 23 for each actuation of a single engaging element is therefore mainly determined by the lateral dimension of the teeth on the rack member. Unfortunately, the size of such step can be too large for some applications. In particular, in medical applications, accurate placement of a medical aid, such as a needle guide, is crucial. For some applications it is therefore desirable to realize slowing.

Figure 5A:
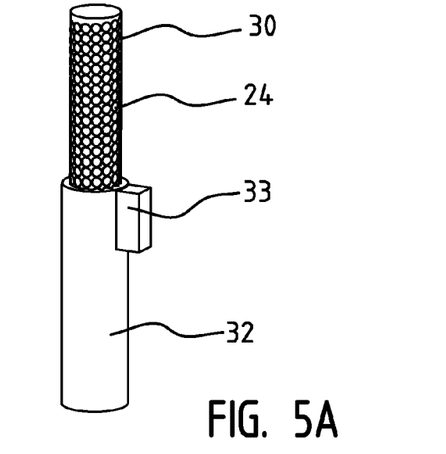
FIGS. 5A-5G illustrate an actuator of the motor according to the invention.
Figure 5B:
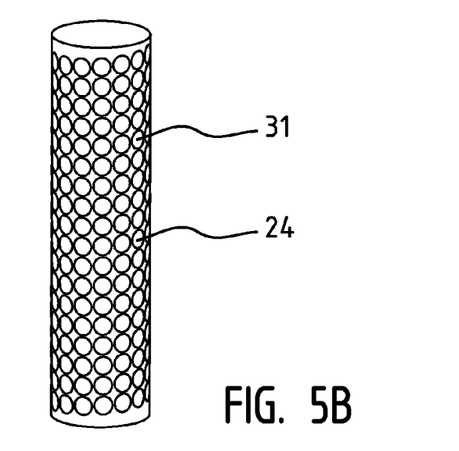

The slowing can be realized with the rack member as shown in FIG. 5A and FIG. 5B. A cylindrical rack member 30 is provided with conical holes 24 in spiral manner for the purpose of forming a periodic structure. Rack member 30 moves through a tooth member comprising a motor housing 32, preferably made of plastic, embodied as a tubular element. This element accommodates three piston-type cylinders placed in a compartment 33 in motor housing 32. The cylinders are connected to conical teeth which fit in conical holes 24 in rack member surface 31, similar to the embodiment of FIG. 4. The cylinders are placed to one side in the longitudinal direction of the tubular element. This is done in order to push aside the clearance necessary to allow the various parts to move, so that it does not occur in the arm.

Movement of the rack member in two directions is determined when the teeth are activated. The cylinders are placed such that rack member 30, when activated, does not move in linear direction but describes a helical movement in accordance with the helical path of the conical holes 24 around cylindrical rack member 30. As such, the axial displacement obtained after a full rotation of rack member 30 corresponds to the heart-to-heart distance 34 of the conical holes 24 in the axial direction. By varying the diameter of rack member 30, and thereby the number of holes, a large number of different transmissions can be realized.

As discussed in conjunction with FIG. 4A, the arrangement of the conical holes and engaging elements can be chosen differently to allow motion in different directions. For instance, instead of a helical distribution, the holes can be distributed in a circular manner. Also in this case, simultaneous rotation and translation can be obtained because also here multiple directions of periodicity exist.

Figure 5C:
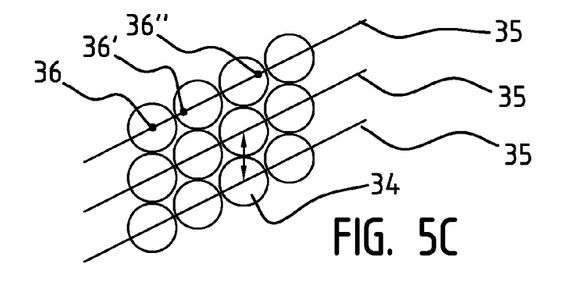

FIG. 5C is a schematic view of conical holes 34 describing a spiral 35 around rack member 30 in an exaggerated manner. The spiral is shown in a flat plane in FIG. 5C. The individual actuators, and in particular the engaging elements thereof, are arranged so as to engage rack member 30 at a position on spiral 35 with a mutual phase difference of 120 degrees relative to the periodic structure on rack member 30. Dots 36 correspond here to the projection of the tooth ends along the direction of engagement of the teeth on gear rack surface 31. It is noted here that these points each lie on the spiral associated with the tooth.

The motor can further be provided with a second set of actuators for instance arranged along the axial direction of rack member 30. Using these cylinders, rack member 30 can move in the axial direction without rotation and more swiftly than by using the earlier mentioned first set of actuators. Hence, by using different sets, different movements can be achieved, i.e. rotation, translation, and a combination thereof.

It should be noted that the embodiment in FIG. 5 can be modified such that rack member 30 is arranged in a through hole of motor housing 32. Consequently, rack member 30 can move through motor housing 32 to emerge at the other side. As such, the dynamical range of rack member 30, i.e. the range of axial displacement thereof, is greatly improved.

FIGS. 5D-5G show a partially open perspective view of the embodiment of FIG. 5A, wherein the different actuators have been shifted in circumferential direction for better displaying the operation.

Figure 5D:
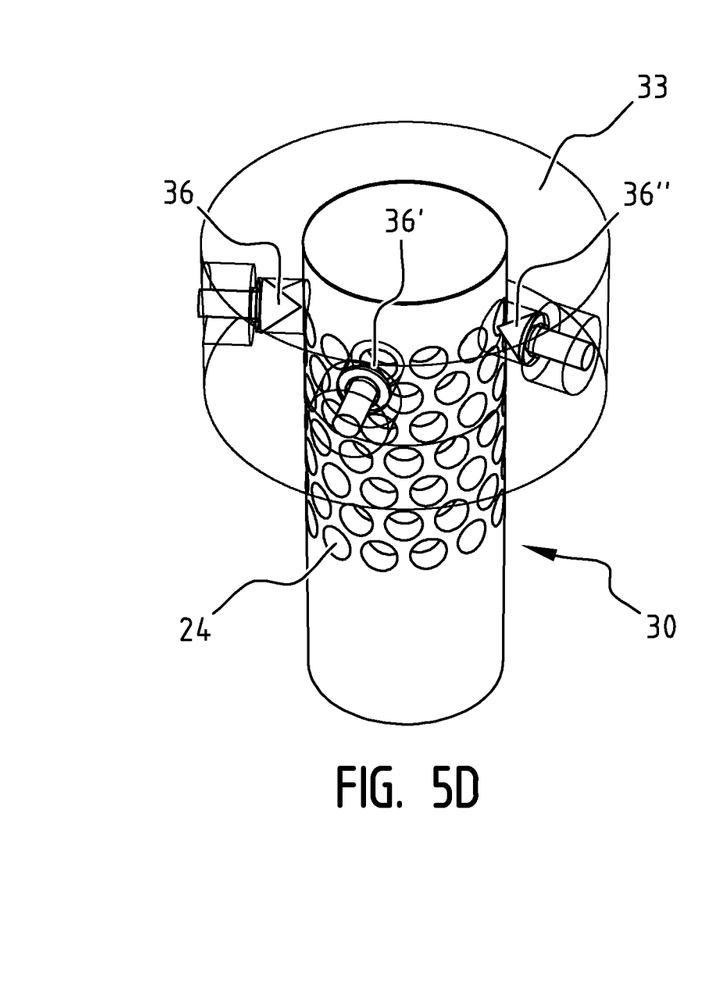

In FIG. 5D, none of the engaging elements, which are referred to as 36-36", engage a conical hole 24. In such a mode, and in absence of a locking means, rack member 30 can move axially with respect to motor housing 32.

Figure 5E:
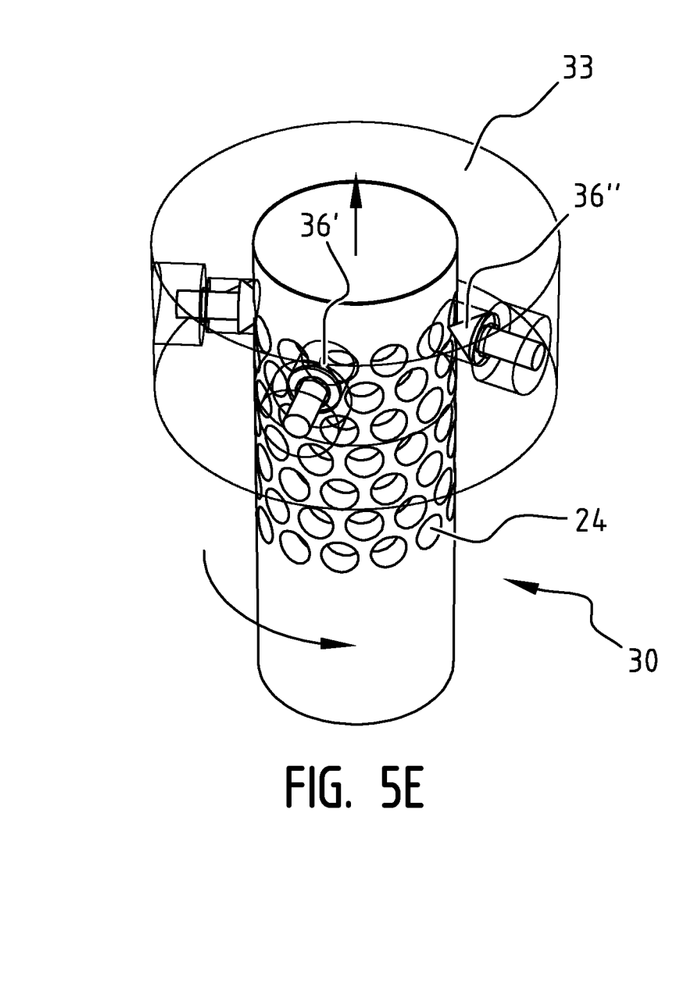

In FIG. 5E, engaging element 36, which, like the other engaging elements, is connected to a piston rod of a pneumatic or hydraulic cylinder (not shown), is pushed into a conical hole 24. Because this hole is not fully aligned with engaging element 36, a net force will be developed in the circumferential and/or axial direction causing rack member 30 to move accordingly as indicated by the arrows.

Next, the pneumatic or hydraulic cylinder corresponding to engaging element 36 will be deactivated, or this cylinder will actively withdraw engaging element 36. In the latter case, the control unit controlling the various actuators will need to be able to reverse the actuating motion of the hydraulic or pneumatic cylinders. In other words, in addition to controlling the extending stroke, it will need to be able to control the retracting stroke in a periodic manner similar to the extending stroke and taking into account the timing of controlling the other actuators.

Figure 5F:
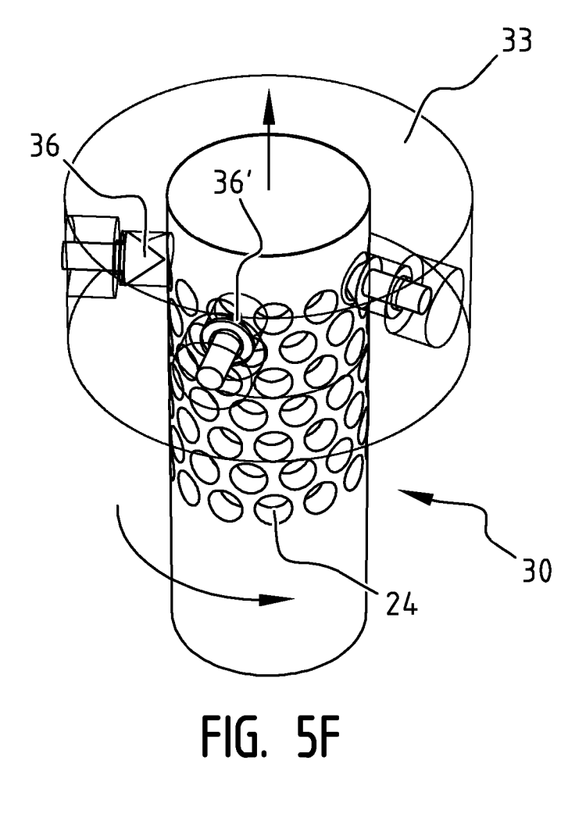

After or concurrently with engaging element 36 retracting from the relevant conical hole, engaging element 36" is brought into engagement with a conical hole, see FIG. 5F. This will again cause an axial and/or circumferential movement. The same as described above is repeated for engaging element 36', see FIG. 5G.

Figure 5G:
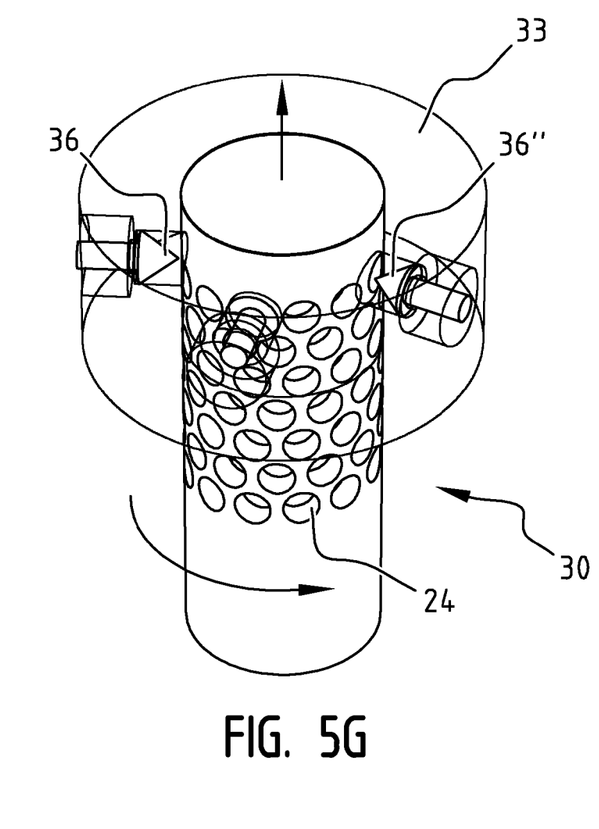

Once engaging element 36' is fully inserted in the conical hole it opposes, the position of engaging element 36 relative to the conical hole it is directed to is the same as that depicted in FIG. 5D. This allows the same sequence of motions to be repeated, thereby obtaining a single continuous motion.

Figure 6:
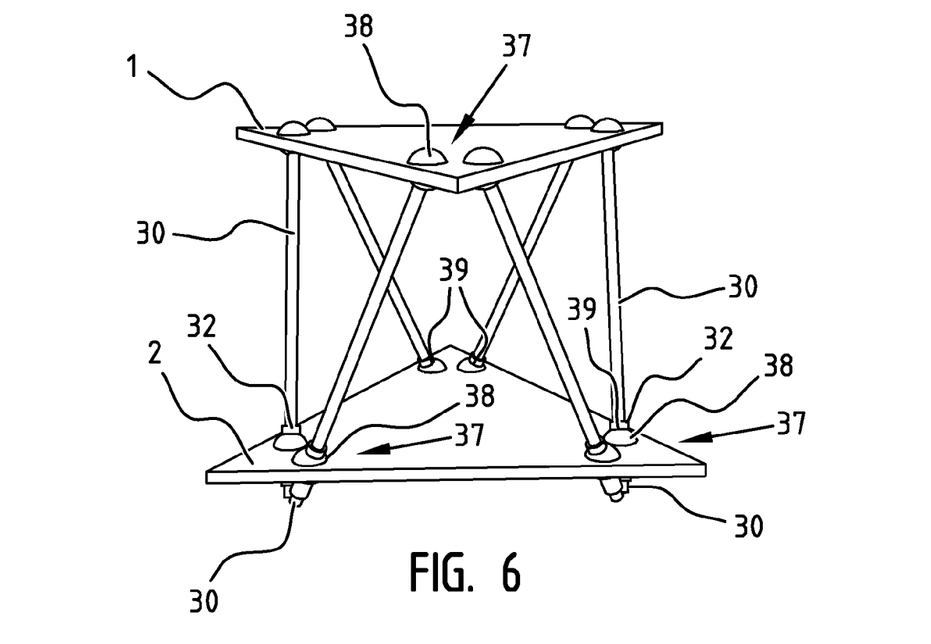
FIG. 6 shows a variation of the robot arm device of FIG. 1.

FIG. 6 shows a variation of the robot arm device of FIG. 1. Here, first frame part 2 is provided with through holes 37 in which a ball joint 38 is mounted. Ball joint 38 facilitates the connection between tooth member 32 and first frame part 2. To that end, ball joint 38 is itself provided with a through hole 39 in which tooth member 32 is fixedly connected. In particular if tooth member 32 is also arranged with a through hole as described, a versatile robot arm device is achieved. Because the legs, i.e. the motors, between first 2 and second 3 frame part can be made very small, the robot arm device has a very high dynamic range.

Figure 7:
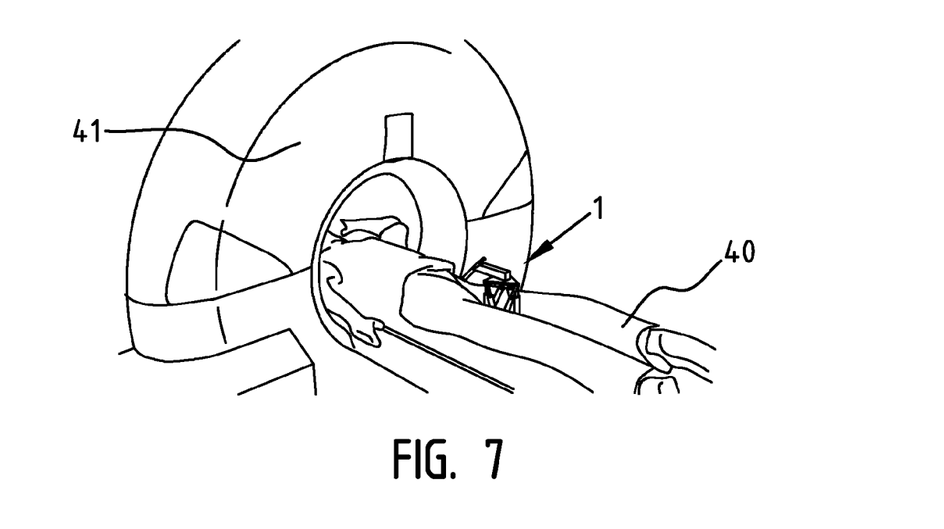
FIG. 7 shows an application of the robot arm device according to the present invention.

FIG. 7 shows an application of the robot arm device according to the invention. The device is mounted here on a bed in the vicinity of a patient 40. The robot arm device and the needle guide placed hereon are placed in an initial position. An MRI image is then recorded using MRI scanner 41.

It is important to note that no metal objects may be placed in the vicinity of the MRI scanner. This reduces the choice of components and materials for realizing the robot arm device. In FIG. 7, pneumatic cylinders are used as actuators in the motors and each component of the robot arm device is made from non-magnetic, non-magnetisable, and non-conductive material.

The activation of the pneumatic cylinders takes place remotely by means of electropneumatic valves. When the physician places the robot arm device near the patient and makes rough settings, it is desirable to be able to regulate blocking and unblocking of the robot arm device from there. This takes place with control keys on the device itself. These are valves in the form of keys, wherein pressure is, or is not, applied to conduits connected to the valves. The pressure in the conduits is detected remotely, i.e. away from the MRI environment, where the detection results are used to supply compressed air to the pneumatic cylinders.

The pneumatic cylinders are preferably driven by means of compressed air. Because a displacement of about only three millimeters is required per cylinder, the air consumption is zero. A small, quiet compressor is therefore sufficient. Each cylinder has its own thin compressed air line, which are bundled and connected to a compressed air unit. This unit comprises a compressor, pressure regulators, pressure sensors, a vacuum pump, electropneumatic valves and the electronics for converting computer signals into usable actuation of the electropneumatic valves.

The electropneumatic valves are actuated by the compressed air unit in order to obtain the desired movement. The movements of the robot arm device, which moves by changing leg length, are not linear. That is, the extension of a determined leg can have different effects on the position of the robot arm device, depending on the position of the other legs. This non-linearity is mathematically predictable however, and is compensated by software. The distance over which the displacement will take place can be predicted by the use of the motors according to the present invention. It will therefore be possible with the robot arm device to describe a definable path. By coupling the MRI and the robot arm device it is possible to appear within a determined section once the location and state of the robot arm device have been established. If a structure which is recognisable on MRI (for instance the needle guide) is controlled by the robot arm device and it can be seen on screen, a sequence of the motors actuated by the compressed air unit can determine exactly where the robot arm device is situated and which extension or arm is being used.

After manual manipulation of the robot arm device the position and state of the robot arm device are for instance no longer known. A recognition procedure is then required. One or more motors receive for instance twenty pulses in a determined direction. The exact position of the first frame part and the state of the robot arm device can be derived from the displacement of the needle guide, as can the relative position of second frame part and arm. Once this is known, any displacement of the needle guide can be predicted and regulated by the compressed air unit.

It should be understood by the skilled person that various modifications to the embodiments described herein can be made without departing from the scope of the invention which is defined by the following claims.

The invention claimed is:

1. A motor system, comprising a motor and a control unit, said motor comprising:
   a rack member provided with a periodic structure on a surface thereof, said periodic structure having a periodic arrangement of elements, wherein the rack member has a body with a substantially cylindrical shape with the periodic arrangement on a circumferential surface of said cylinder, said gear elements being distributed in a helical path around said cylindrical shape;
   a tooth member accommodating a set of multiple actuators, each of said actuators comprising an engaging element shaped for engaging a respective gear element and a drive unit for driving said engaging element to move back and forth with respect to said periodic structure, wherein each engaging element engages said respective gear element at least during part of its movement towards said respective gear element to cause a relative movement between said rack member and said tooth member, and wherein each of said actuators is positioned spaced apart to engage said periodic structure at a different wrapped phase thereof, wherein the tooth member comprises a housing provided with a circular opening for receiving at least part of said rack member, and wherein the set of actuators is arranged in a radial direction with respect to said rack member, wherein the arrangement of the engaging elements and the arrangement of the gear elements is configured to allow a simultaneous rotation and translation of the rack member relative to the housing; and
   wherein the control unit is configured for periodically controlling each drive unit of each actuator in the set of actuators to operate in a time-shifted manner with respect to each other to cause said simultaneous rotation and translation of the rack member.

2. The motor system according to claim 1, wherein the gear elements are periodically arranged completely around said body.

3. The motor system according to claim 1, wherein the circular opening is formed by a circular through hole in said housing.

4. The motor system according to claim 1, wherein the control unit is arranged to control the drive units within the set of actuators such that at least one powered engaging element engages the surface structure at each point in time during operation of the motor.

5. The motor system according to claim 1, wherein the drive unit of each actuator is configured to operate in a powering state for powering said engaging element to move towards said rack member and in a release state for movement of said engaging element away from the rack member, said drive unit comprising a resilient member at least operable in said release state and configured for urging the engaging element to move away from the rack member and/or the drive unit being configured to allow the engaging element to move away from the rack member in the release state essentially without exerting a force on the engaging element.

6. The motor system according to claim 1, wherein the gear element comprises a conical cavity in the surface of said rack member and wherein the engaging element has a corresponding conical protrusion.

7. The motor system according to claim 1, comprising at least n actuators belonging to the set, wherein n is larger than or equal to two, and wherein the respective actuators are positioned to engage the surface structure at a wrapped phase of approximately m ×360/n, wherein m =1. . .n, respectively.

8. The motor system according to claim 1, wherein the drive unit comprises an actuable piston-type cylinder, said actuable cylinder having a cylinder housing and a piston movable therein, wherein said engaging element is arranged on an end of said piston.

9. A robot arm device, comprising:
   a first frame part which can be mounted or placed on a support for the robot arm device;
   a second frame part coupled to the first frame part;
   a motor system as defined by claim 1 for changing at least one of the mutual orientation and distance of the first and second frame parts, wherein said tooth member of said motor of said motor system is coupled to one of said first and second frame part, and wherein the rack member is coupled to the other of said first and second frame part.

10. The robot arm device according to claim 9, wherein the robot arm device comprises at least six of said motor systems, wherein the motor systems and the first and second frame parts form a Stewart platform.

11. The robot arm device according to claim 9, wherein at least one of the first and the second frame part is provided with a through hole for receiving the tooth member or the rack member of the motor of the motor system therein.

12. The robot arm device according to claim 11, comprising a hinge, having a through hole provided therein in which said tooth member or said rack member is fixedly connected to said hinge, wherein the hinge is arranged for hingedly connecting said tooth member or said rack member to said at least one of the first and second frame part.

13. The robot arm device according to claim 12, wherein the hinge comprises a ball joint.

* * * * *